(12) United States Patent
Trail et al.

(10) Patent No.: US 10,879,028 B2
(45) Date of Patent: Dec. 29, 2020

(54) BEAM POSITION MONITORS FOR MEDICAL RADIATION MACHINES

(71) Applicant: Varian Medical Systems, Inc., Palo Alto, CA (US)

(72) Inventors: Mark E. Trail, Menlo Park, CA (US); James E. Clayton, Saratoga, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 635 days.

(21) Appl. No.: 15/098,759

(22) Filed: Apr. 14, 2016

(65) Prior Publication Data

US 2017/0296844 A1 Oct. 19, 2017

(51) Int. Cl.
*H01J 35/14* (2006.01)
*H01J 35/04* (2006.01)
(Continued)

(52) U.S. Cl.
CPC ............... *H01J 35/14* (2013.01); *G21K 1/08* (2013.01); *H01J 1/26* (2013.01); *H01J 1/38* (2013.01);
(Continued)

(58) Field of Classification Search
CPC ........ H01J 1/00; H01J 1/46; H01J 1/88; H01J 1/94; H01J 1/96; H01J 3/00; H01J 3/02; H01J 3/027; H01J 3/029; H01J 3/10; H01J 3/12; H01J 3/26; H01J 3/28; H01J 3/30; H01J 3/36; H01J 3/38; H01J 7/44; H01J 21/00; H01J 21/02; H01J 21/06; H01J 21/10; H01J 21/16; H01J 19/00; H01J 19/28; H01J 19/38; H01J 19/42; H01J 19/46; H01J 19/48; H01J 19/50; H01J 19/78; H01J 19/82; H01J 31/00; H01J 31/02; H01J 31/04; H01J 35/00; H01J 35/02; H01J 35/025; H01J 35/04; H01J 35/14; H01J 35/24; H01J 35/30; H01J 2235/00; H01J 2235/02; H01J 2235/06; H01J 29/00; H01J 29/003; H01J 29/02; H01J 29/025; H01J 29/46; H01J 29/48; H01J 29/485; H01J 29/54; H01J 29/56; H01J 29/563; H01J 29/58; H01J 29/62; H01J 29/70; H01J 29/72; H01J 29/74;
(Continued)

(56) References Cited

U.S. PATENT DOCUMENTS 2,307,212 A * 1/1943 Goldsmith ............ H01J 29/54
313/429
2,640,948 A * 6/1953 Burrill .................... A23L 3/263
164/DIG. 4

(Continued)

*Primary Examiner* — Anastasia Midkiff
(74) *Attorney, Agent, or Firm* — Vista IP Law Group, LLP

(57) ABSTRACT

An apparatus includes: a structure having a lumen for accommodating a beam (e.g., electron beam, proton beam, or a charged particle beam), wherein the structure is a component of a medical radiation machine having a target for interaction with the beam to generate radiation; and a first beam position monitor comprising a first electrode and a second electrode, the first electrode being mounted to a first side of the structure, the second electrode being mounted to a second side of the structure, the second side being opposite from the first side; wherein the first beam position monitor is located upstream with respect to the target.

33 Claims, 8 Drawing Sheets

(51) Int. Cl.
| | |
|---|---|
| *H01J 19/42* | (2006.01) |
| *H01J 31/02* | (2006.01) |
| *H01J 19/38* | (2006.01) |
| *H01J 35/30* | (2006.01) |
| *G21K 1/08* | (2006.01) |
| *H05G 1/26* | (2006.01) |
| *H05G 1/30* | (2006.01) |
| *H01J 29/54* | (2006.01) |
| *H01J 1/46* | (2006.01) |
| *H01J 29/46* | (2006.01) |
| *H01J 29/70* | (2006.01) |
| *H01J 1/26* | (2006.01) |
| *H01J 1/38* | (2006.01) |
| *H01J 29/02* | (2006.01) |
| *H01J 1/88* | (2006.01) |
| *H01J 29/56* | (2006.01) |
| *H01J 37/147* | (2006.01) |
| *H01J 29/82* | (2006.01) |
| *H01J 37/063* | (2006.01) |
| *A61N 5/10* | (2006.01) |

(52) U.S. Cl.
CPC .............. *H01J 1/46* (2013.01); *H01J 1/88* (2013.01); *H01J 19/38* (2013.01); *H01J 19/42* (2013.01); *H01J 29/02* (2013.01); *H01J 29/46* (2013.01); *H01J 29/54* (2013.01); *H01J 29/56* (2013.01); *H01J 29/70* (2013.01); *H01J 29/82* (2013.01); *H01J 29/826* (2013.01); *H01J 31/02* (2013.01); *H01J 35/04* (2013.01); *H01J 35/30* (2013.01); *H01J 37/063* (2013.01); *H01J 37/147* (2013.01); *H05G 1/26* (2013.01); *H05G 1/30* (2013.01); *A61N 5/1048* (2013.01); *A61N 2005/1095* (2013.01); *H01J 2229/58* (2013.01); *H01J 2237/04* (2013.01); *H01J 2237/083* (2013.01); *H01J 2237/15* (2013.01); *H01J 2237/1501* (2013.01); *H01J 2237/248* (2013.01)

(58) Field of Classification Search
CPC ........ H01J 29/82; H01J 29/823; H01J 29/826; H01J 29/96; H01J 29/98; H01J 37/00; H01J 37/02; H01J 37/04; H01J 37/06; H01J 37/063; H01J 37/065; H01J 37/147; H01J 37/1471; H01J 37/1472; H01J 37/24; H01J 2229/00; H01J 2229/0007; H01J 2229/0046; H01J 2229/48; H01J 2229/481; H01J 2229/4824; H01J 2229/4827; H01J 2229/4831; H01J 2229/58; H01J 2229/582; H01J 2237/00; H01J 2237/02; H01J 2237/03; H01J 2237/032; H01J 2237/036; H01J 2237/04; H01J 2237/049; H01J 2237/06; H01J 2237/061; H01J 2237/063; H01J 2237/06375; H01J 2237/0835; H01J 2237/15; H01J 2237/1501; H01J 2237/1504; H01J 2237/151; H01J 2237/248; H01J 2237/2485; H01J 2237/2487; H01J 2893/00; H01J 2893/0001; H01J 2893/0002; H01J 2893/0005; H01J 2893/0006; H01J 2893/0008; H01J 2893/0009; H01J 2893/0011; H01J 2893/0012; H01J 2893/0029; H01J 2893/003; H01J 2893/0048; H01J 2893/0049; H01J 2893/0051; H01J 2893/0058; H05G 1/08; H05G 1/26; H05G 1/30; H05G 1/52; G21K 1/00; G21K 1/08; G21K 1/087; H05H 7/00; H05H 7/001; H05H 7/22; H05H 9/00; H05H 9/04; H05H 15/00; H05H 2007/007; H05H 2007/008; H05H 2277/00; H05H 2277/10; H05H 2277/11

See application file for complete search history.

(56) References Cited

U.S. PATENT DOCUMENTS

| | | | | | |
|---|---|---|---|---|---|
| 2,904,721 | A | * | 9/1959 | Ault | G11C 11/23 313/419 |
| 3,293,429 | A | * | 12/1966 | Leboutet | G01T 1/29 219/121.23 |
| 3,555,347 | A | * | 1/1971 | Dickinson | H01J 29/54 219/121.13 |
| 3,609,445 | A | * | 9/1971 | Williams | G09G 1/00 315/369 |
| 3,749,963 | A | * | 7/1973 | Frederickson | H05H 5/02 219/121.28 |
| 3,838,284 | A | * | 9/1974 | McIntyre | A61N 5/1048 250/385.1 |
| 3,955,089 | A | * | 5/1976 | McIntyre | A61N 5/1048 250/385.1 |
| 3,975,640 | A | * | 8/1976 | Boux | G21K 1/08 250/385.1 |
| 4,075,489 | A | * | 2/1978 | Neal | A61B 6/032 378/10 |
| 4,184,968 | A | * | 1/1980 | Stauffer | G02B 7/30 250/201.8 |
| 4,588,891 | A | * | 5/1986 | Saito | H01J 37/28 250/310 |
| 4,803,368 | A | * | 2/1989 | Barthelmes | G01T 1/185 250/374 |
| 5,459,393 | A | * | 10/1995 | Tanaka | G01T 1/29 315/500 |
| 5,672,878 | A | * | 9/1997 | Yao | G01T 1/185 250/385.1 |
| 6,218,675 | B1 | * | 4/2001 | Akiyama | A61N 5/1043 250/396 ML |
| 6,288,401 | B1 | * | 9/2001 | Chang | H01J 29/54 250/396 R |
| 6,873,931 | B1 | * | 3/2005 | Nower | G01B 11/272 702/151 |
| 6,975,895 | B1 | * | 12/2005 | Pelc | H01J 35/14 378/137 |
| 8,890,100 | B2 | * | 11/2014 | Huntzinger | G21K 1/10 250/503.1 |
| 9,155,911 | B1 | * | 10/2015 | Balakin | A61N 5/1081 |
| 9,188,685 | B2 | * | 11/2015 | Takayanagi | A61N 5/1048 |
| 2005/0099145 | A1 | * | 5/2005 | Nishiuchi | H05H 7/06 315/500 |
| 2007/0014392 | A1 | * | 1/2007 | Madey | H05G 2/00 378/119 |
| 2009/0149735 | A1 | * | 6/2009 | Fallone | A61N 5/1049 600/411 |
| 2012/0294424 | A1 | * | 11/2012 | Chin | A61N 5/1042 378/65 |
| 2013/0301805 | A1 | * | 11/2013 | Hemberg | H01J 35/08 378/137 |
| 2014/0126704 | A1 | * | 5/2014 | Zou | H01J 35/025 378/197 |
| 2015/0352376 | A1 | * | 12/2015 | Wiggers | A61B 6/545 250/252.1 |

* cited by examiner

BEAM POSITION MONITORS FOR MEDICAL RADIATION MACHINES

FIELD

The field of the application relates to medical radiation machines, and more particularly, to systems and methods for monitoring beam position in medical radiation machines.

BACKGROUND

Radiation therapy involves medical procedures that selectively deliver high doses of radiation to certain areas inside a human body. A radiation machine for providing radiation therapy includes an electron source that provides electrons, and an accelerator that accelerates the electrons to form an electron beam. The electron beam is delivered downstream where it strikes a target to generate radiation. The radiation is then collimated to provide a radiation beam having a certain desired characteristic for treatment purpose.

In accordance with one or more embodiments described herein, a system and a method for monitoring a position of electron beam in medical radiation machine are provided.

SUMMARY

An apparatus includes: a structure having a lumen for accommodating a beam (e.g., electron beam, proton beam, or a charged particle beam), wherein the structure is a component of a medical radiation machine that has a target for interaction with the beam to generate radiation; and a first beam position monitor comprising a first electrode and a second electrode, the first electrode being mounted to a first side of the structure, the second electrode being mounted to a second side of the structure, the second side being opposite from the first side; wherein the first beam position monitor is located upstream with respect to the target.

Optionally, the apparatus further includes circuitry configured to obtain signals from the first and second electrodes at every period that is anywhere from 0.01 nanosecond to 10 microseconds.

Optionally, the beam has a pulse duration, and wherein the apparatus further comprises circuitry configured to obtain signals from the first and second electrodes at every period that is a fraction of the pulse duration of the beam.

Optionally, the apparatus further includes a processing unit configured to perform processing of signals obtained from the first electrode and the second electrode, wherein the processing unit is configured to determine a position of the beam based on the signals from the first electrode and the second electrode.

Optionally, the processing unit is also configured to determine at least a part of a cross-sectional shape of the beam based at least in part on the signals received from the first and second electrodes.

Optionally, the processing unit is configured to move the beam, to adjust a shape of the beam, or both, based on the determined position of the beam.

Optionally, the processing unit is configured to adjust an operation of the accelerator based on the determined position of the beam.

Optionally, the apparatus further includes a second beam position monitor coupled to the structure.

Optionally, the first beam position monitor is configured to provide first signals for monitoring a first position of the beam along a first axis, and wherein the second position monitor is configured to provide second signals for monitoring a second position of the beam along a second axis that is different from the first axis.

Optionally, the second beam position monitor comprises a third electrode and a fourth electrode, the third electrode being mounted to a third side of the structure, the fourth electrode being mounted to a fourth side of the structure, the fourth side being opposite from the third side.

Optionally, the apparatus further includes a third position monitor having a fifth electrode and a sixth electrode, wherein the third position monitor is downstream with respect to the first and second beam position monitors.

Optionally, the apparatus further includes a fourth position monitor having a seventh electrode and an eighth electrode, wherein the fourth position monitor is downstream with respect to the first and second beam position monitors.

Optionally, the apparatus further includes a processing unit configured to determine a first coordinate of a first cross section of the beam based on first signals from the first position monitor and second signals from the second position monitor; wherein the processing unit is also configured to determine a second coordinate of a second cross section of the beam based on third signals from the third position monitor and fourth signals from the fourth position monitor.

Optionally, the processing unit is further configured to determine an orientation of the beam based on the first and second coordinates.

Optionally, the first beam position monitor is connected to a daughter card.

Optionally, the apparatus further includes a second beam position monitor that is downstream from the first beam position monitor.

Optionally, the first electrode and the second electrode are aligned along a first radial axis that is perpendicular to a longitudinal axis of the lumen, and wherein the second beam position monitor comprises a third electrode and a fourth electrode aligned along a second radial axis that is different from the first radial axis.

Optionally, the first radial axis and the second radial axis form a 45° angle.

Optionally, the first radial axis and the second radial axis form a 90° angle.

Optionally, the apparatus further includes a beam-bender for bending the beam, wherein the first beam position monitor is coupled upstream with respect to the beam-bender, and wherein the second beam position monitor is coupled to the beam-bender or downstream with respect to the beam-bender.

Optionally, the apparatus further includes a first amplifier coupled to the first electrode, and a second amplifier coupled to the second electrode.

Optionally, the first amplifier is configured to provide a first logarithmic response, and wherein the second amplifier is configured to provide a second logarithmic response.

Optionally, the apparatus further includes a processing unit is configured to subtract the second logarithmic response from the first logarithmic response.

Optionally, the first position monitor comprises a log-ratio beam position monitor, such as a Bergoz log-ratio beam position monitor.

Optionally, the structure is a part of an accelerator, a transmission line, or a beam-bender.

A method of monitoring a position of a beam at a medical radiation machine that includes an accelerator and a target for interaction with the beam to generate radiation, includes: obtaining a first signal from a first electrode; obtaining a second signal from a second electrode, wherein the first electrode and the second electrode are on first opposite sides of a space in the medical radiation machine through which the beam is being delivered; and processing the first signal and the second signal to determine a first position of the beam; wherein the first electrode and the second electrode are parts of a first position monitor, and wherein the first position monitor is located upstream with respect to the target.

Optionally, the first position of the beam comprises a value of a coordinate.

Optionally, the method further includes: obtaining a third signal from a third electrode; obtaining a fourth signal from a fourth electrode; wherein the third electrode and the fourth electrode are on second opposite sides of the space through which the beam is being delivered; and processing the third signal and the fourth signal to determine a second position of the beam.

Optionally, the first position of the beam comprises a first value, and the second position of the beam comprises a second value, and wherein the first value and the second value form a first coordinate for the beam.

Optionally, the first coordinate is for a cross section of the beam.

Optionally, the method further includes: obtaining a fifth signal from a fifth electrode; obtaining a sixth signal from a sixth electrode; wherein the fifth electrode and the sixth electrode are downstream with respect to the first position monitor; and processing the fifth signal and the sixth signal to determine a third position of the beam.

Optionally, the method further includes: obtaining a seventh signal from a seventh electrode; obtaining a eighth signal from an eighth electrode; wherein the seventh electrode and the eighth electrode; and processing the seventh signal and the eighth signal to determine a fourth position of the beam.

Optionally, the third position of the beam comprises a third value, and the fourth position of the beam comprises a fourth value, and wherein the third value and the fourth value form a second coordinate for the beam.

Optionally, the method further includes determining an orientation of the beam based on the first and second coordinates.

Optionally, the method further includes adjusting the beam based at least in part on the determined first position of the beam.

Optionally, the signals are obtained from the first and second electrodes at every period that is anywhere from 1 nanosecond to 10 microseconds.

Optionally, the beam has a pulse duration, and wherein the signals are obtained from the first and second electrodes at every period that is a fraction of the pulse duration of the beam.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
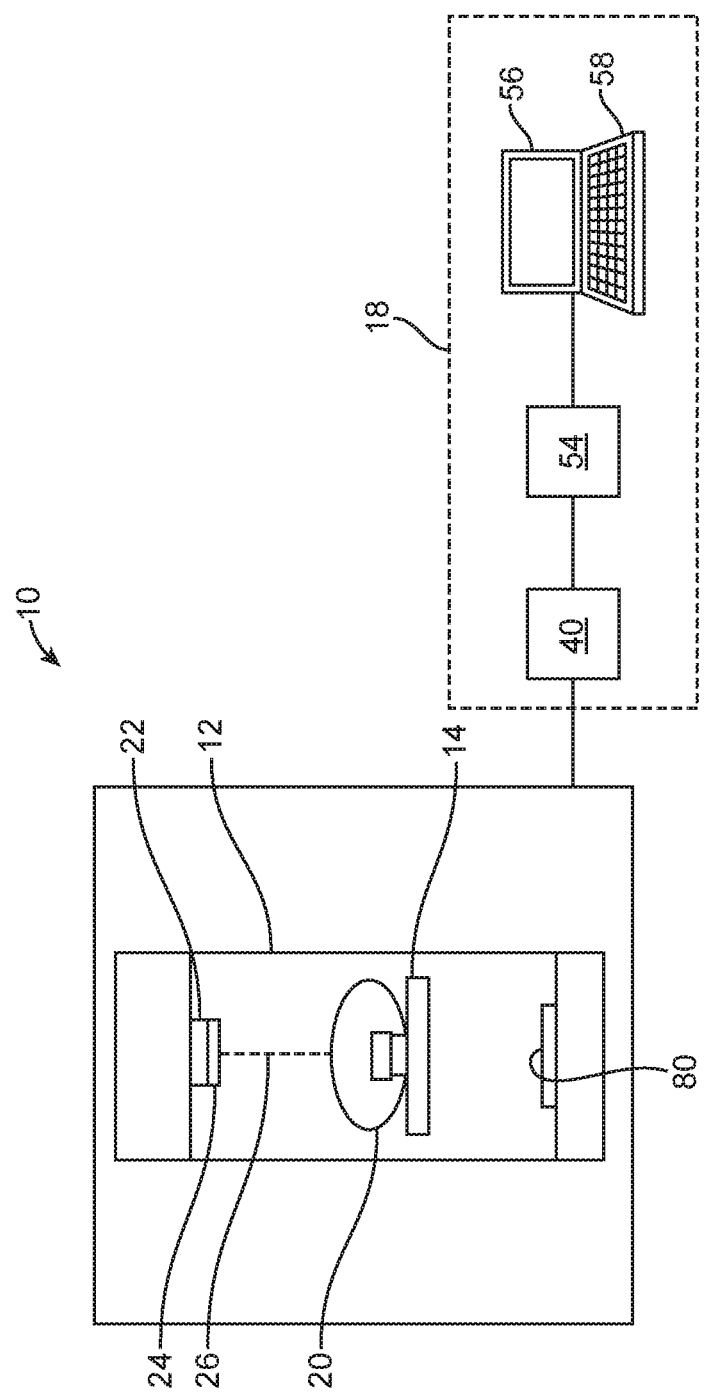
FIG. 1 illustrates a radiation treatment system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate a proton beam, electron beam, or neutron beam, as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purposes. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

Figure 2:
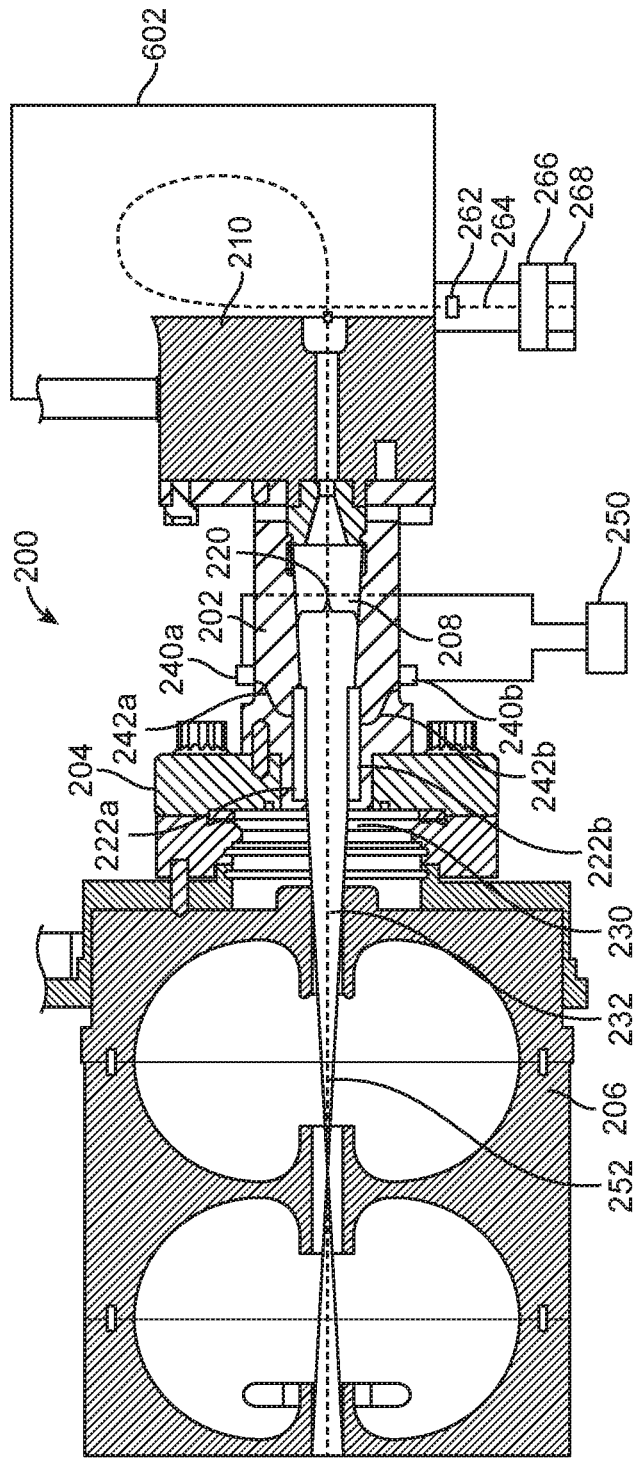
FIG. 2 illustrates a beam position monitor being used with an accelerator.

FIG. 2 shows an apparatus 200 that includes a beam position monitor in accordance with some embodiments. The apparatus 200 includes a structure 202 having a first end 204 configured for coupling to a part of an accelerator 206, and a lumen 208 (e.g., beam tube) extending from the first end 204, wherein the structure 202 is a component of a medical radiation machine (the system 10 of FIG. 1). As used in this specification, the term "lumen" may be any space or cavity in a structure. The accelerator 206 is configured to receive electrons from an electron gun, and is configured to accelerate the electrons to form an electron beam 252. The electron beam 252 is transmitted to an orbit chamber 210, which is a part of a beam-bender 602 for bending (turning) the beam 252 into a desired orientation. The beam 252 then strikes a target 262 to form radiation 264. The radiation 264 travels into an ion chamber 266 in which radiation dose is measured. The radiation 264 then exits through an output portion 268, which may be the radiation source 22, or at least a part of the radiation source 22 of FIG. 1. The accelerator 206, the beam-bender 602, and the ion chamber 266 are all parts of the system 10 of FIG. 1.

In the illustrated embodiments shown in FIG. 2, the lumen 208 allows the electron beam 252 to travel therethrough. The apparatus 200 includes a first beam position monitor 220 comprising a first electrode 222a and a second electrode 222b, the first electrode 222a being mounted to a first side of the structure 202, the second electrode 222b being mounted to a second side of the structure 202, the second side being opposite from the first side. In the illustrated embodiments, the first and second electrodes 222a, 222b of the first beam position monitor 220 are mounted to an interior surface of the structure 202, and are facing the lumen 208. In some cases, the surfaces of the electrodes 222a, 222b are flushed with adjacent interior surfaces of the structure 202. In other cases, the surfaces of the electrodes 222a, 222b may be raised, or recessed, with respect to the adjacent interior surfaces of the structure 202.

As shown in the figure, the first beam position monitor 220 is located upstream with respect to the ion chamber 266 or upstream with respect to the target 262. Such configuration obviates the need to use any sensor at the ion chamber 266 for inferring position of the electron beam 252 upstream from the ion chamber 266, which may not be accurate, and may not reflect the true position of the beam. In particular, a position of the beam upstream from the ion chamber 266 may be derived using information obtained from the sensor at the ion chamber 266. In one technique, the sensor at the ion chamber 266 may provide information for determining a beam position at the ion chamber 266. A change in the beam position upstream from the ion chamber 266 may cause a corresponding change in the position at the ion chamber 266. However, such technique is not as desirable because the true position of the beam upstream from the ion chamber 266 is not directly measured, but is inferred by the positional correspondence derived using ion chamber sensor.

In the illustrated example, the first beam position monitor 220 is located downstream from an opening 230 at the accelerator 206. In other cases, the first beam position monitor 220 may be located at the accelerator 206. For example, the first beam position monitor 220 may be located anywhere along the length of the lumen 232 in the accelerator 206. In such cases, the accelerator 206 itself may be considered to be a "structure" to which the first beam position monitor 220 is mounted. Also, in other embodiments, the first beam position monitor 220 may be located anywhere upstream from the target 262.

As shown in FIG. 2, the apparatus 200 also includes a first output 240a coupled to the first electrode 222a via a first conductor 242a, and a second output 240b coupled to the second electrode 222b via a second conductor 242b. The conductors 242a, 242b are housed within the structure 202, and extend across the walls of the structure 202 to reach the first and second outputs 240a, 240b, respectively. The first and second outputs 240a, 240b are signal-pickup locations outside the structure 202, and may be in the form of electrode pads or any of other types of electrical connections.

The apparatus 200 further includes a processing unit 250 configured to obtain signals from the first and second outputs 240a, 240b, and to process the signals to determine a position of electron beam 252. In other embodiments, the processing unit 250 may not be a part of the apparatus 200.

In some cases, the outputs 240a, 240b (and optionally also the processing unit 250) may be considered to be parts of a circuitry configured to obtain signals from the first and second electrodes 222a, 222b. In some embodiments, the circuitry may be configured to obtain signals at every period that is anywhere from 0.01 nanosecond to 10 microseconds, and more preferably anywhere from 1 nanosecond to 10 microseconds. In other embodiments, the beam 252 has a pulse duration, and the circuitry may be configured to obtain signals from the first and second electrodes 222a, 222b at every period that is a fraction of the pulse duration of the beam 252. Such configuration allows the position of the beam 252 to be determined sufficiently fast with respect to the pulse frequency of the beam 252.

Figure 3:
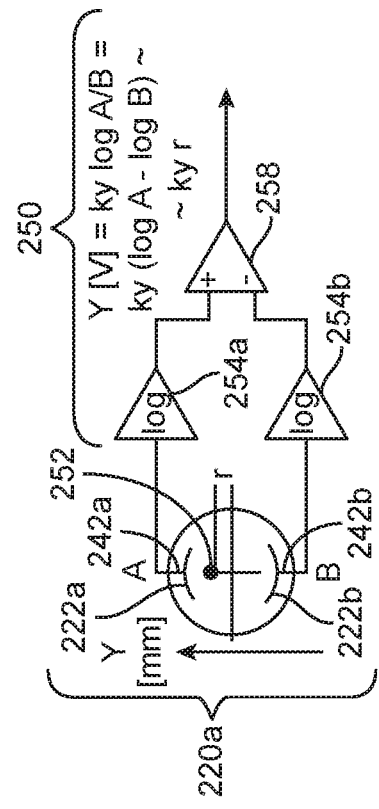
FIG. 3 illustrates an implementation of the beam position monitor of FIG. 2, and its associated circuitry.

As discussed, the processing unit 250 may be configured to determine the position of a beam based on the signals from the first electrode 222a and the second electrode 222b. FIG. 3 illustrates an example of an implementation of the processing unit 250. As shown in the figure, the processing unit 250 may include a first amplifier 254a coupled to the first electrode 222a, and a second amplifier 254b coupled to the second electrode 222b. The first amplifier 254a may be configured to provide a first logarithmic response, and the second amplifier 254b is configured to provide a second logarithmic response. In other cases, the amplifiers 254a, 254b may provide other types of responses that may or may not be logarithmic responses. Also, in other cases, the amplifiers 254a, 254b are optional, and the processing unit 250 may not include the amplifiers 254a, 254b. As shown in the figure, the processing unit 250 may also include a subtractor 258 configured to subtract the second logarithmic response from the first logarithmic response to determine a position of the beam 252. In the illustrated example, because the first and second electrodes 222a, 222b are located along a Y-axis across the lumen 208 through which the beam 252 is travelling, the determined position of the beam 252 will be a value representing a Y-coordinate of the beam 252—i.e., the position of the beam 252 along the Y-axis that is transverse (e.g., 90°) with respect the longitudinal axis of the accelerator 206 or the structure 202.

Various techniques may be used to obtain information based on signals from the electrodes 222 for determining a beam position. For example, in some cases, the maximum value of the signals from the electrode 222 may be used. In such cases, a first maximum value may be derived from signals from the first electrode 222a, and a second maximum value may be derived from signals from the second electrode 222b. The beam position may then be determined based on a difference of the first and second maximum values, or a difference of the logarithmic responses of the first and second maximum values. In other cases, an average value of the signals from the electrode 222 may be used. In further cases, one or more extreme maximum value(s) and/or minimum value(s) may be removed from the set of signals obtained from the electrode 222. Then the maximum value or an average value of the remaining signals may be used. In still further cases, an average of the signals within a certain standard deviation from the mean or median value of the set of signals may be used. Other techniques for deriving a value from a set of the signal values may be used.

During use, as the beam 252 travels through the accelerator 206 and the structure 202, charges induced by the beam 252 are picked up by the electrodes 222a, 222b. The electrodes 222a, 222b transmit signals corresponding to these charges to the processing unit 250 via the conductors 242a, 242b. The processing unit 250 then determines the position of the beam 252 based on these signals. As shown in the example of FIG. 3, because the beam 252 is located closer to the first electrode 222a, the first electrode 222a will have more induced charges from the beam 252 compared to the second electrode 222b. As a result, the response from the first amplifier 254a will be higher than the response from the second amplifier 254b. After the subtractor 258 subtracts the second response from the first response, the result will correspond with, or will represent, the position of the beam 252 along the Y-axis. In some cases, the result may be multiplied by a constant $k_y$ to obtain a true position of the beam 252 along the Y-axis.

In some cases, the processing unit 250 may also be configured to determine at least a part of a cross-sectional shape of the beam 252 based at least in part on the signals received from the first and second electrodes 222a, 222b. For example, in some embodiments, each of the first and second electrodes 222a, 222b is configured to detect a distribution of charges induced by the beam 252, and information regarding such distribution is transmitted to the processing unit 250. Based on the manner in which the charges are distributed in each of the first and second electrodes 222a, 222b, the processing unit 250 can determine at least a partial shape of the cross section of the beam 252.

In some cases, the processing unit 250 may be a part of a beam control system, or may be communicatively coupled to a beam control system, that is configured to move the beam 252, to adjust a shape of the beam 252, or both, based on the determined position of the beam 252. For example, if the processing unit 250 determines that the beam 252 is too close to the first electrode 222a, the processing unit 250 may then generate a control signal to cause the beam 252 to be steered away from the first electrode 222a so that the beam 252 may be closer to the center between the first and second electrodes 222a, 222b. For example, the control signal may activate one or more electromagnets to interact with the electron beam to thereby move the electron beam in a certain direction. Also, the processing unit 250 may be configured to adjust an operation of the accelerator 206 based on the determined position of the beam 252. For example, the processing unit 250 may operate the accelerator 206 to stop the beam 252, to decelerate the beam 252, to accelerate the beam 252, or any combination of the foregoing.

Figure 4A:
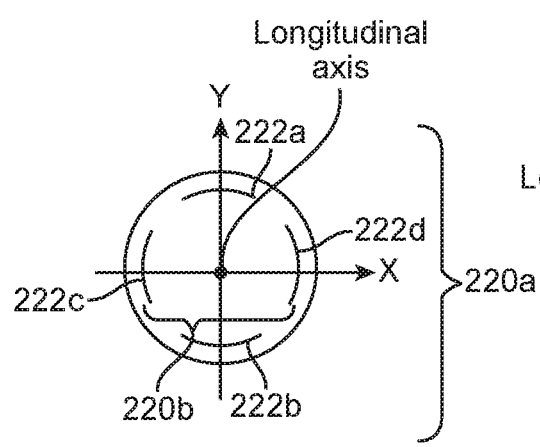
FIG. 4A illustrates two beam position monitors.

In the above embodiments, the apparatus 200 has been described with reference to determining a position of the beam 252 along an axis that is transverse (e.g., perpendicular) to the longitudinal axis of the accelerator. In other embodiments, the apparatus 200 may optionally further include a second beam position monitor coupled to the structure 202. FIG. 4A illustrates an apparatus 200 that has a first beam position monitor 220a, and a second beam position monitor 220b. The first beam position monitor 220a includes the first and second electrodes 222a, 222b. The second beam position monitor 220b includes a third electrode 222c and a fourth electrode 222d. As shown in the figure, the third electrode 222c is mounted to a third side of the structure 202, the fourth electrode 222d being mounted to a fourth side of the structure 202, the fourth side being opposite from the third side. Thus, all four electrodes 222a-222d are mounted on different respective sides of the structure 202.

In some embodiments, all four electrodes 222a-222d may be located at the same longitudinal position along the longitudinal axis of the accelerator 206 or the structure 202. In other embodiments, the second beam position monitor 220b may be offset with respect to the first beam position monitor 220a along the longitudinal axis of the accelerator 206 or the structure 202. For example, the center-to-center distance between the first and second beam position monitors 220a, 220b may be anywhere from 0.5 inch to 24 inches, and more preferably, from 0.5 inch to 12 inches, and even more preferably, from 0.5 inch to 6 inches.

In the illustrated example, the circumferential positions (i.e., the positions around the lumen 208 through which the beam 252 travels) of the electrodes 222a, 222b of the first beam position monitor 220a is different from the circumferential positions of the electrodes 222c, 222d of the second beam position monitor 220b. In particular, the first electrode 222a and the second electrode 222b of the first beam position monitor 220a are aligned along a first radial axis that is perpendicular to a longitudinal axis of the accelerator 206/structure 202, and the electrodes 222c, 222d of the second beam position monitor are aligned along a second radial axis that is perpendicular to the first radial axis when viewed along the longitudinal axis of the accelerator 206/structure 202.

The first beam position monitor 220a is configured to provide first signals for monitoring a first position of the beam 252 along a first axis (e.g., a first radial axis that is perpendicular to the longitudinal axis of the accelerator 206), and wherein the second position monitor 220b is configured to provide second signals for monitoring a second position of the beam 252 along a second axis (e.g., a second radial axis that is perpendicular to the longitudinal axis of the accelerator 206) that is different from the first axis. In the illustrated example shown in FIG. 4A, the first beam position monitor 220a is configured to provide signals for determining a Y-position of the beam 252 along the Y-axis (radial axis), and the second beam position monitor 220b is configured to provide signals for determining a X-position of the beam 252 along the X-axis (radial axis that is perpendicular to the Y-axis). After the processing unit 250 determines the X-position and the Y-position of the beam 252, these two values may be grouped to form a two-dimensional position (e.g., a coordinate x, y) of the beam 252. Thus, as used in this specification, the term "position" may refer to a one-dimensional position (e.g., a position along an axis), or a two-dimensional position (e.g., an x-y coordinate).

Figure 4B:
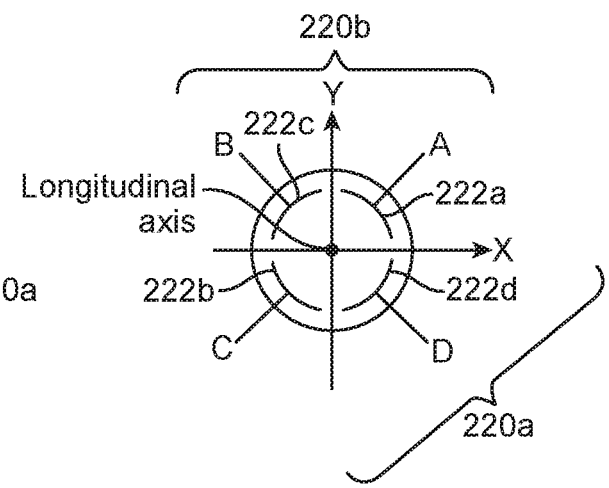
FIG. 4B illustrates another variation of two beam position monitors.

In other embodiments, the axes along which the beam positions are being monitored may be arbitrary. For example, as shown in FIG. 4B, the first and second electrodes 222a, 222b may be rotated 45° so that they are along an a radial axis (line A-C) that is 45° with respect to the X-axis. Similarly, the third and fourth electrodes 222c, 222d may be rotated 45° so that they are along a radial axis (line B-D) that is perpendicular to that associated with the first and second electrodes 222a, 222b.

Figure 4C:
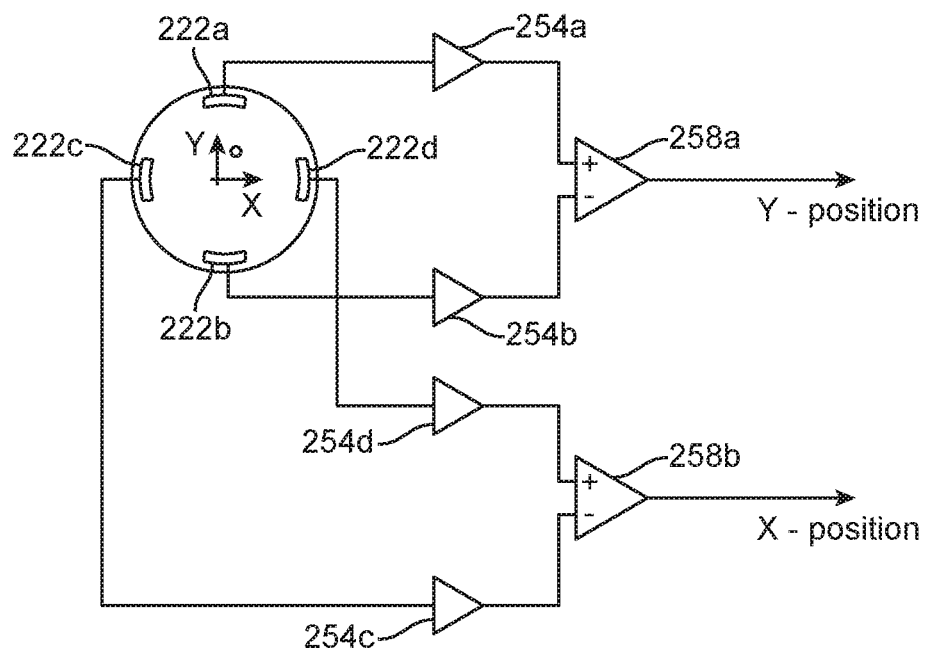
FIG. 4C illustrates the two beam position monitors of FIG. 4A and their associated circuitry.

It should be noted that in the examples of FIGS. 4A and 4B, each of the beam position monitors 220a, 220b may have its own set of circuitry like that shown in FIG. 3. For example, as shown in FIG. 4C, the first position monitor 220a has associated first circuitry that includes first and second amplifiers 254a, 254b and a first subtractor 258a. Also, the second position monitor 220b has associated second circuitry that includes third and fourth amplifiers 254c, 254d, and a second subtractor 258b. The first circuitry provides signals for determining a first position (e.g., Y-position) of the beam 252 and the second circuitry provides signals for determining a second (e.g., X-position) of the beam 252.

In some cases, the processing unit 250 may also be configured to determine at least a part of a cross-sectional shape of the beam 252 based at least in part on the signals received from the electrodes 222a-222d. For example, in some embodiments, each of the electrodes 222a-222d is configured to detect a distribution of charges induced by the beam 252, and information regarding such distribution is transmitted to the processing unit 250. Based on the manner in which the charges are distributed in each of the electrodes 222a-222b, the processing unit 250 can determine at least a partial shape of the cross section of the beam 252.

In some cases, the processing unit 250 may be a part of a beam control system, or may be communicatively coupled to a beam control system, that is configured to move the beam 252, to adjust a shape of the beam 252, or both, based on the determined position (e.g., two-dimensional position with x-y coordinate) of the beam 252. For example, if the processing unit 250 determines that the beam 252 is too close to the first electrode 222a, the processing unit 250 may then generate a control signal to cause the beam 252 to be steered away from the first electrode 222a so that the beam 252 may be closer to the center between the first and second electrodes 222a, 222b. Also, the processing unit 250 may be configured to adjust an operation of the accelerator 206 based on the determined position of the beam 252. For example, the processing unit 250 may operate the accelerator 206 to stop the beam 252, to decelerate the beam 252, to accelerate the beam 252, or any combination of the foregoing.

In some cases, the amplifiers 254a, 254b and/or the subtractor 258 may be considered to be separate from the processing unit 250. For example, the amplifiers 254a, 254b and/or the subtractor 258 may be considered to be part(s) of the beam position monitor 220.

In some embodiments, the first and second beam position monitors 220a, 220b may be located at the structure 202, which may be a part of a transmission line. In other embodiments, the first and second beam position monitors 220a, 220b may be located at the accelerator 206. In further embodiments, the first and second beam position monitors 220a, 220b may be located at other places that are downstream with respect to the accelerator 206.

As illustrated in the above embodiments, the beam position monitor(s) implemented upstream with respect to the ion chamber 266 or the target 262 is advantageous. Such configuration obviates the need to use any sensor at the ion chamber 266 for inferring position of the electron beam 252 upstream from the ion chamber 266, which may not be accurate, and may not reflect the true position of the beam 252. In particular, sensors may be implemented at the ion chamber 266 for sensing signals associated with the radiation beam 264. The sensed signals may then be processed to determine a position of the radiation beam 264 at the ion chamber 266. The position of the radiation beam 264 may then be used to infer the position of the electron beam 252 upstream from the ion chamber 266. However, such technique may not be as desirable compared to the technique described with reference to the embodiments of FIGS. 2-4, because it does not directly measure the true position of the electron beam 252. On the other hand, the embodiments described herein use beam position monitor(s) that provides direct measurement of the electron beam position in the accelerator beam line. Also, sensors at an ion chamber 266 may require 2-10 msec period between pulses to provide the information. By the time the sensors at the ion chamber 266 provides information for inferring the position of the electron beam 252 that is at some distance from the sensors, the inferred position may be significantly different from the actual position of the electron beam 252. If the inferred position is used to control the beam position, it may result in large symmetry and dose errors. The embodiments of the beam position monitoring described herein eliminate these problems.

Furthermore, the ion chamber 266 is used for dose calculation. Any failure of the ion chamber 266 (e.g., failure of the ability to respond to fast asymmetry, dose-drift, target failure, etc.) may result in undetectable radiation delivery errors. Thus, the ion chamber 266 may potentially be a single-point-of-failure in terms of obtaining beam positions. Accordingly, the embodiments described herein may be used with the sensors at the ion chamber 266 to provide a level of redundant safety. Alternatively, the embodiments described herein may be used solely to determine beam position.

In addition, the embodiments of the beam position monitoring described herein are advantageous because they allow beam position(s) to be directly measured at certain location (s) along the beam line. This in turn allows the processing unit 250 to effectively and accurately control the accelerator 206 and/or the beam steering mechanism to achieve any desirable adjustment because there is no delay of waiting for the electron beam 252 to travel downstream to the ion chamber 266, and no delay for waiting for any sensors at the ion chamber 266 to provide signals for position determination. Also, the control of the accelerator 206 and/or the beam steering mechanism is based on direct position measurement of the electron beam 252, and is not based on some inferred position of the beam 252 based on some signals derived downstream from the beam 252. As a result, the embodiments described herein may allow a more accurate delivery of radiation dose, and may improve treatment efficiency. In some cases, hypofractionated treatment may be achieved.

Figure 5:
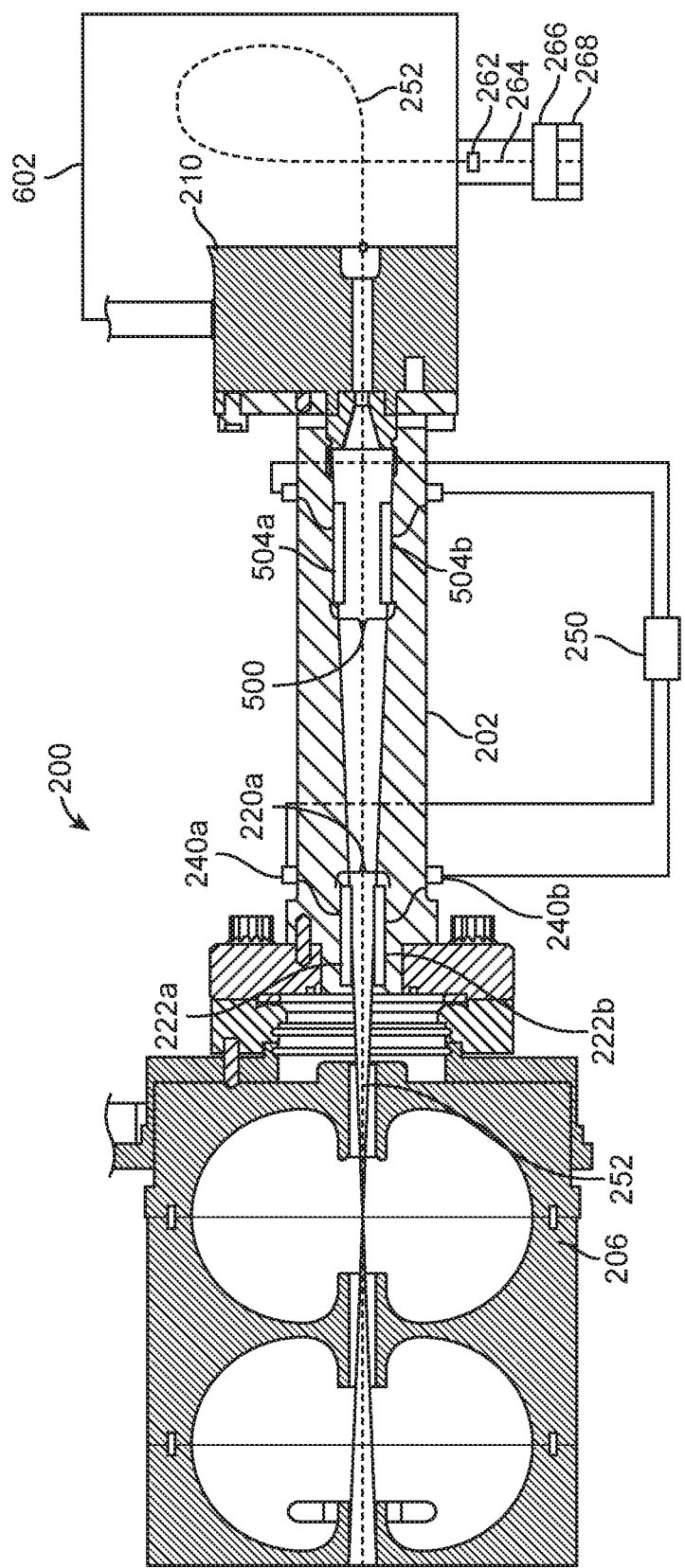
FIG. 5 illustrates an accelerator with transmission line having multiple beam position monitors.

In some embodiments, the apparatus 200 may further include an additional beam position monitor spaced at some minimal prescribed distance from the first beam position monitor 220a. FIG. 5 illustrates an apparatus 200 that is the same as that described with reference to FIG. 2, except that the apparatus 200 further includes an additional beam position monitor 500. The additional beam position monitor 500 includes electrodes 504a, 504b coupled to opposite sides of the structure 202. The configuration of the additional beam position monitor 500 may be the same or similar to that of the first beam position monitor 220a.

It should be noted that the additional bream position monitor 500 is not limited to being placed at the illustrated location, and may be placed at other locations in other embodiments. For example, in other embodiments, the additional beam position monitor 500 may be placed inside the accelerator 206, or at another structure that is coupled to the accelerator 206 or to the structure 202.

In the illustrated embodiments shown in FIG. 5, the first beam position monitor 220a provides a set of signals for allowing the processing unit 250 to determine a position (e.g., P1) of the beam 252. The additional beam position monitor 500 provides an additional set of signals for allowing the processing unit 250 to determine a position (e.g., P2) of the beam 252 that is away from the position P1 determined using the first beam position monitor 220a. In some embodiments, the processing unit 250 may be configured to use one of the positions P1, P2 as a redundancy value to check the other one of the positions P1, P2.

In some embodiments, the additional beam position monitor 500 may be considered to be a "second" beam position monitor that is in addition to the first beam position monitor 220a. In other embodiments, if the apparatus 200 has two beam position monitors 220a, 220b for determining a first two-dimensional (e.g., x-y) position of the beam 252, like that described with reference to FIG. 4A/4B, then the additional beam position monitor 500 may be considered to be a "third" beam position monitor that is in addition to the first and second beam position monitors 220a, 220b. In such cases, the electrodes 504a, 504b may be referred to as the fifth and sixth electrodes 504a, 504b. In further embodiments, the apparatus 200 may also include a fourth beam position monitor. In such cases, the electrodes of the fourth beam position monitor may be referred to as the seventh and eighth electrodes. Also, in such cases, the first and second beam position monitors 220a, 220b provide signals for determining a first two-dimensional position P1 (e.g., x-y coordinate) of the beam 252, while the third and fourth beam position monitors provide signals for determining a second two-dimensional position P2 of the beam 252 that is away from the first two-dimensional position. The two positions P1, P2 are for two respective cross sections of the beam 252 at two different locations along the longitudinal axis of the accelerator 206 or the structure 202. In some embodiments, the processing unit 250 may be configured to use one of the positions P1, P2 as a redundancy value to check the other one of the positions P1, P2. Alternatively, or additionally, the processing unit 250 may be configured to determine an orientation of the beam 252 based on the first and second positions P1, P2 (coordinates). For example, the processing unit 250 may determine an angle between the beam line (e.g., a line between the positions P1, P2) and the longitudinal axis of the accelerator 206.

In some cases, the third and fourth beam position monitors may be downstream with respect to the first and second beam position monitors 220a, 220b. For example, the third and fourth beam position monitors may be at the structure 202, or at the beam-bender 602 (which may be considered a "structure" as well). In other cases, the third and fourth beam position monitors may be upstream with respect to the first and second beam position monitors 220a, 220b. For example, the third and fourth beam position monitors may be implemented at the accelerator 206 (which may also be considered a "structure").

Also, in some embodiments, the circumferential positions (i.e., the positions around the lumen 208 through which the beam 252 travels) of the electrodes of the first and second beam position monitors 220a, 220b may be the same as the circumferential positions of the electrodes of the third and fourth beam position monitors. For example, the first electrode 222a and the second electrode 222b of the first beam position monitor 220a may be aligned along a first radial axis that is perpendicular to a longitudinal axis of the lumen 208, and wherein the electrodes of the third beam position monitor may be aligned along a second radial axis that is in the same direction as the first radial axis but offset along the longitudinal axis of the accelerator 206/structure 202.

Figure 4D:
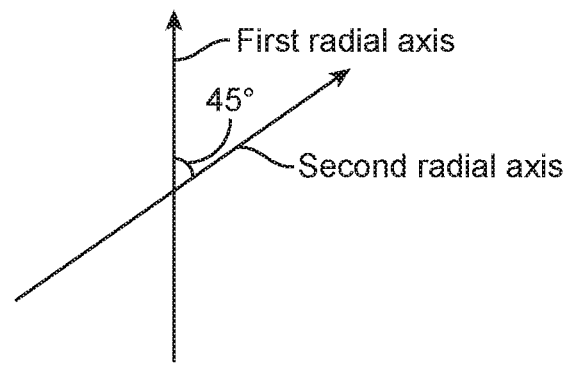
FIG. 4D illustrates first radial axis and second radial axis forming a 45° angle.
Figure 4E:
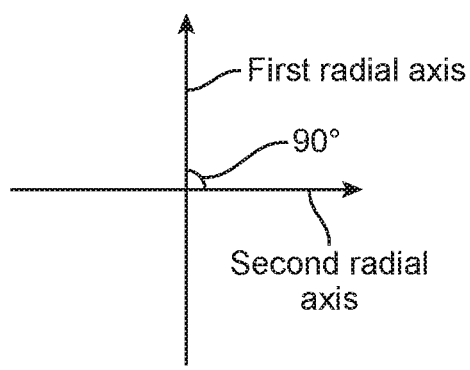
FIG. 4E illustrates first radial axis and second radial axis forming a 90° angle.

In other embodiments, the circumferential positions of the electrodes of the first and second beam position monitors 220a, 220b may be different from the circumferential positions of the electrodes of the third and fourth beam position monitors. For example, the first electrode 222a and the second electrode 222b of the first beam position monitor 220a may be aligned along a first radial axis that is perpendicular to a longitudinal axis of the lumen 208, and wherein the electrodes of the third beam position monitor may be aligned along a second radial axis that is in a different direction from the first radial axis and is offset along the longitudinal axis of the accelerator 206/structure 202. In some cases, the first radial axis and the second radial axis form a 45° angle (FIG. 4D). In other cases, the first radial axis and the second radial axis may form other angles (such as 90° angle shown in FIG. 4E).

Figure 6:
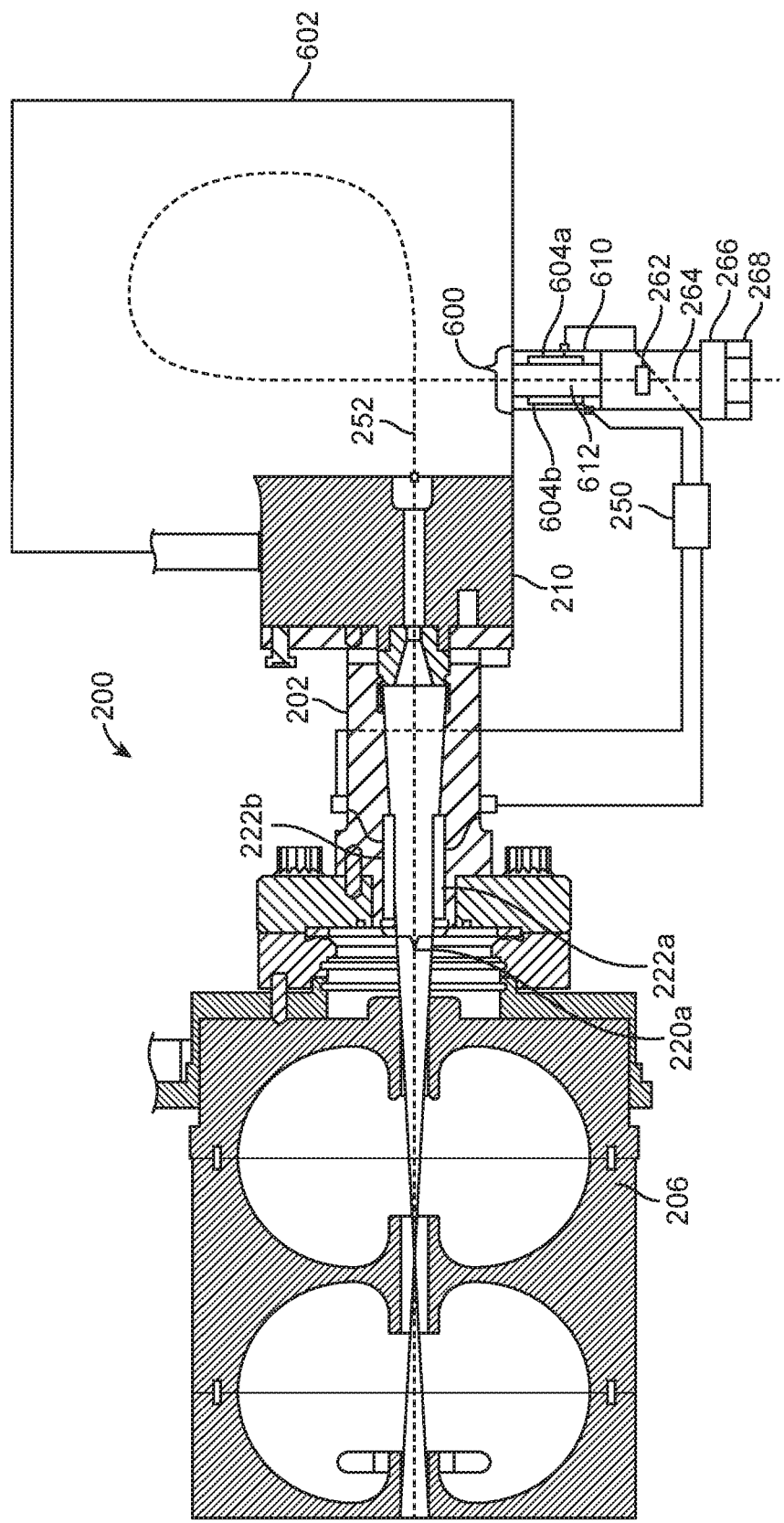
FIG. 6 illustrates another accelerator with a beam-bender for beam bending, particular showing multiple beam position monitors.

In some embodiments, the apparatus 200 may further include an additional beam position monitor at or coupled to a beam-bender for bending the beam 252. FIG. 6 illustrates an apparatus 200 that is the same as that described with reference to FIG. 2, except that the apparatus 200 further includes an additional beam position monitor 600. The additional beam position monitor 600 includes electrodes 604a, 604b coupled to opposite sides of a structure 610. The structure 610 has a lumen 612 that allows the beam 252 to travel therein after the beam 252 has been bent (steered) by a beam-bender 602. The beam-bender 602 includes multiple bending magnets configured to bend the beam 252 so that it can be steered to a desired direction. The configuration of the additional beam position monitor 600 may be the same or similar to that of the first beam position monitor 220a. In some cases, the structure 610 may be considered to be a part of the beam-bender 602. In other cases, the structure 610 may be considered to be a separate device from that of the beam-bender 602.

It should be noted that the additional bream position monitor 600 is not limited to being placed at the illustrated location, and may be placed at other locations in other embodiments. For example, in other embodiments, the additional beam position monitor 600 may be placed inside the beam-bender 602, or may be placed downstream with respect to the beam-bender 602. If the additional beam position monitor 600 is downstream with respect to the beam-bender 602, the additional beam position monitor 600 may be at a structure, like the structure 610 shown in the figure, or at another structure that is coupled indirectly to the beam-bender 602 through other component(s).

In the illustrated embodiments shown in FIG. 6, the first beam position monitor 220a is coupled upstream with respect to the beam-bender 602, and the additional beam position monitor 600 is coupled to the beam-bender 602 or downstream with respect to the beam-bender 602. The additional beam position monitor 600 provides an additional set of signals for allowing the processing unit 250 to determine a position of the beam 252 at or downstream from the beam-bender 602. In some embodiments, the processing unit 250 may be configured to correlate the position (e.g., position P1 as determined using the additional beam position monitor 600) of the beam 252 at or downstream from the beam-bender 602, with the position (e.g., position P2 as determined using the first beam position monitor 220a) of the beam 252 upstream from the beam-bender 602. For example, the processing unit 250 may determine that a change of P1 by a first amount will cause a corresponding change of P2 by a second amount. In some embodiments, the processing unit 250 may be configured to determine an amount of beam position adjustment based on both the position P1 of the beam 252 upstream from the beam-bender 602, and the position P2 of the beam 252 at or downstream from the beam-bender 602. For example, the processing unit 250 may determine the amount A of beam position adjustment based on some weighted factors for the positions P1, P2, such as: $A = k1*fn(P1) + k2*fn(P2)$, where each of k1 and k2 may be a value that is anywhere from 0 to 1. In some cases, $k2 = 1 - k1$.

In some cases, the processing unit 250 may be a part of a beam control system, or may be communicatively coupled to a beam control system, that is configured to move the beam 252, to adjust a shape of the beam 252, or both, based on the determined positions P1, P2 of the beam 252. Also, the processing unit 250 may be configured to adjust an operation of the accelerator 206 based on the determined positions P1, P2 of the beam 252. For example, the processing unit 250 may operate the accelerator 206 to stop the beam 252, to decelerate the beam 252, to accelerate the beam 252, or any combination of the foregoing. Furthermore, the processing unit 250 may be configured to adjust (e.g., optimize) a beam spot size based on one or both of the positions P1, P2 of the beam 252.

In some embodiments, the additional beam position monitor 600 may be considered to be a "second" beam position monitor that is in addition to the first beam position monitor 220a. In other embodiments, if the apparatus 200 has two beam position monitors 220a, 220b upstream from the beam-bender 602, like that described with reference to FIG. 4A/4B, then the additional beam position monitor 600 may be considered to be a "third" beam position monitor that is in addition to the first and second beam position monitors 220a, 220b. In such cases, the electrodes 604a, 604b may be referred to as the fifth and sixth electrodes 604a, 604b. In further embodiments, the apparatus 200 may also include a fourth beam position monitor at or downstream from the beam-bender 602. In such cases, the electrodes of the fourth beam position monitor may be referred to as the seventh and eighth electrodes. Also, in such cases, the first and second beam position monitors 220a, 220b provide signals for determining a first two-dimensional position (e.g., x-y coordinate) of the beam 252 that is upstream from the beam-bender 602, while the third and fourth beam position monitors provide signals for determining a second two-dimensional position of the beam 252 that is at or downstream from the beam-bender 602.

Figure 4F:
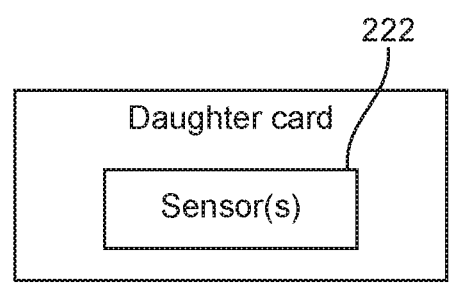
FIG. 4F illustrates a daughter card.

In any of the embodiments described herein, any of the beam position monitors may be connected to (e.g., implemented on) a daughter card (FIG. 4F).

Also, in any of the embodiments described herein, any of the beam position monitor may be implemented using a Bergoz log-ratio beam position monitor.

In addition, in any of the embodiments described herein the input signals from the electrodes of the beam position monitor may be parallel processed. Also, in some cases, the processing may be wideband analog processing.

Furthermore, in some embodiments, each beam position monitor may be configured to provide log signal with 5 MHz bandwidth for analysis by the processing unit 250. In other embodiments, each beam position monitor may be configured to provide other types of signals with other bandwidth values.

In some embodiments, each beam position monitor may be implemented as an electronics module for fast analog processing of signals. In other embodiments, each beam position monitor may have other types of forms and configurations.

In addition, in any of the embodiments described herein, each electrode of the beam position monitor may have a curvilinear surface or a flat (e.g., rectilinear) surface.

Also, in any of the embodiments described herein, the beam position monitor(s) may be configured to monitor the position and/or shape of other types of charged particle beams, such as a proton beam.

Figure 7:
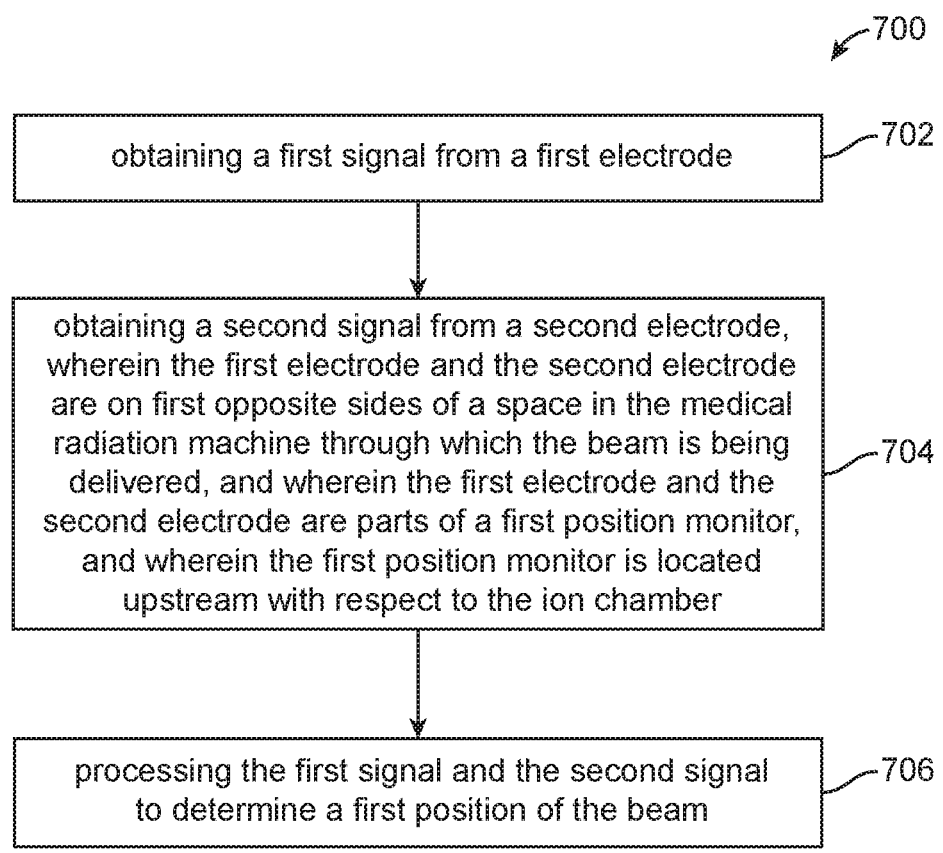
FIG. 7 illustrates a method of monitoring a position of a beam at a medical radiation machine.

FIG. 7 illustrates a method 700 of monitoring a position of a beam at a medical radiation machine that includes an accelerator and an ion chamber. The method 700 includes obtaining a first signal from a first electrode (item 702). The method 700 also includes obtaining a second signal from a second electrode (item 704), wherein the first electrode and the second electrode are on first opposite sides of a space in the medical radiation machine through which the beam is being delivered. The method 700 further includes processing the first signal and the second signal to determine a first position of the beam (item 706). In some cases, the first electrode and the second electrode are parts of a first position monitor, such as the beam position monitor 220 described with reference to FIG. 2. Also, in some cases, the first position monitor is located upstream with respect to the ion chamber or upstream with respect to a target (for interaction with an electron beam to generate radiation).

Optionally, in the method 700 the first position of the beam comprises a value of a coordinate.

Optionally, the method 700 further includes: obtaining a third signal from a third electrode; obtaining a fourth signal from a fourth electrode; wherein the third electrode and the fourth electrode are on second opposite sides of the space through which the beam is being delivered; and processing the third signal and the fourth signal to determine a second position of the beam.

Optionally, in the method 700, the first position of the beam comprises a first value, and the second position of the beam comprises a second value, and wherein the first value and the second value form a first coordinate for the beam.

Optionally, in the method 700, the first coordinate is for a cross section of the beam.

Optionally, the method 700 further includes: obtaining a fifth signal from a fifth electrode; obtaining a sixth signal from a sixth electrode; wherein the fifth electrode and the sixth electrode are downstream with respect to the first position monitor; and processing the fifth signal and the sixth signal to determine a third position of the beam.

Optionally, the method 700 further includes: obtaining a seventh signal from a seventh electrode; obtaining a eighth signal from an eighth electrode; wherein the seventh electrode and the eighth electrode; and processing the seventh signal and the eighth signal to determine a fourth position of the beam.

Optionally, in the method 700, the third position of the beam comprises a third value, and the fourth position of the beam comprises a fourth value, and wherein the third value and the fourth value form a second coordinate for the beam.

Optionally, the method 700 further includes determining an orientation of the beam based on the first and second coordinates.

Optionally, the method 700 further includes adjusting the beam based at least in part on the determined first position of the beam.

Optionally, in the method 700, the signals are obtained from the first and second electrodes at every period that is anywhere from 0.01 nanosecond to 10 microseconds, and more preferably anywhere from 1 nanosecond to 10 microseconds.

Optionally, in the method 700, the beam has a pulse duration, and wherein the signals are obtained from the first and second electrodes at every period that is a fraction of the pulse duration of the beam.

Processing System

Figure 8:
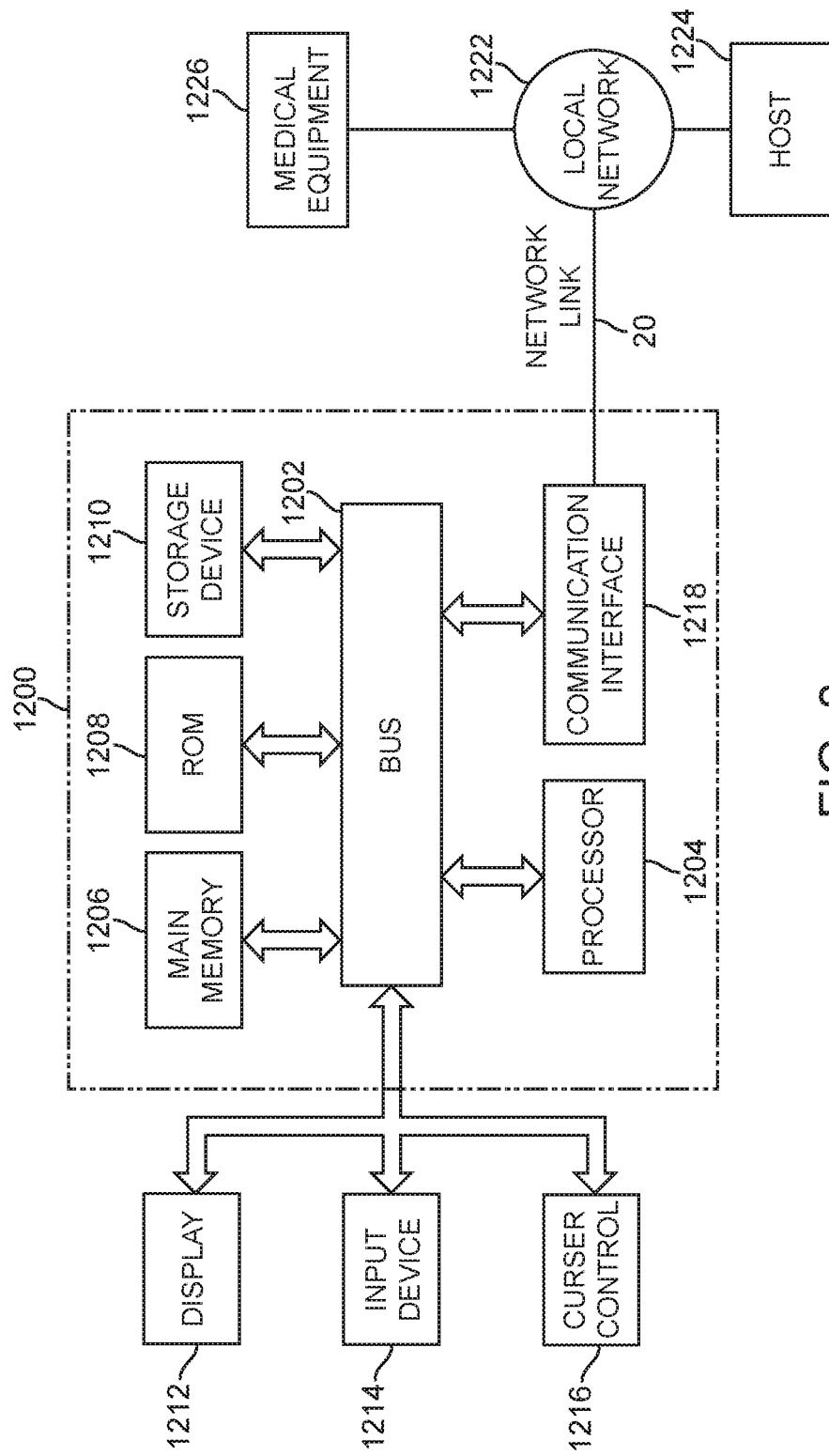
FIG. 8 illustrates a processing system with which embodiments described herein may be implemented.

FIG. 8 is a block diagram that illustrates an embodiment of a processing system 1200 upon which embodiments described herein may be implemented. Processing system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. For example, the processor 1204 may be configured to provide any of the functionalities described with reference to the processing unit 250. In some cases, the processing system 1200 may be used to implement the processor 54 and/or the processing unit 250, or at least parts of these.

Also, in some cases, the processing system 1200 may be a specialized processing system with features and/or functions that are unique and novel.

The processing system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The processing system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The processing system 1200 may be coupled via the bus 1202 to a display 1212, such as a cathode ray tube (CRT), for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The processing system 1200 may be used for performing various functions (e.g., calculation) in accordance with the embodiments described herein. According to one embodiment, such use is provided by processing system 1200 in response to processor 1204 executing one or more sequences of one or more instructions contained in the main memory 1206. Such instructions may be read into the main memory 1206 from another processor-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement features of the embodiments described herein. Thus, embodiments described herein are not limited to any specific combination of hardware circuitry and software.

The term "processor-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. A non-volatile medium may be considered to be an example of a non-transitory medium. Volatile media includes dynamic memory, such as the main memory 1206. A volatile medium may be considered to be another example of a non-transitory medium. Transmission media includes coaxial cables, copper wire and fiber optics, including the wires that comprise the bus 1202. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the processing system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The processing system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the processing system 1200, are exemplary forms of carrier waves transporting the information. The processing system 1200 can send messages and receive data, including program code, through the network(s), the network link 1220, and the communication interface 1218.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An apparatus comprising:
a structure having a lumen for accommodating a beam, wherein the structure is a component of a medical radiation machine having a target for interaction with the beam to generate radiation;
a beam bender located downstream with respect to the structure;
a first beam position monitor comprising a first electrode and a second electrode, the first electrode being mounted to a first side of the structure, the second electrode being mounted to a second side of the structure, the second side being opposite from the first side; and
circuitry configured to obtain signals from the first and second electrodes every 0.01 nanosecond to 10 microseconds;
wherein the first beam position monitor is located upstream with respect to a location where the radiation is generated;
wherein the beam comprises an electron beam; and
wherein the first beam position monitor comprising the first electrode and the second electrode is separated from the beam bender.

2. An apparatus comprising:
a structure having a lumen for accommodating a beam, wherein the structure is a component of a medical radiation machine having a target for interaction with the beam to generate radiation;
a beam bender located downstream with respect to the structure; and
a first beam position monitor comprising a first electrode and a second electrode, the first electrode being mounted to a first side of the structure, the second electrode being mounted to a second side of the structure, the second side being opposite from the first side;
wherein the first beam position monitor is located upstream with respect to a location where the radiation is generated;
wherein the beam comprises an electron beam;
wherein the first beam position monitor comprising the first electrode and the second electrode is separated from the beam bender; and
wherein the beam has a pulse duration, and wherein the apparatus further comprises circuitry configured to obtain signals from the first and second electrodes at every period that is a fraction of the pulse duration of the beam.

3. The apparatus of claim 1, further comprising a processing unit configured to perform processing of signals obtained from the first electrode and the second electrode, wherein the processing unit is configured to determine a position of the beam based on the signals from the first electrode and the second electrode.

4. The apparatus of claim 3, wherein the processing unit is also configured to determine at least a part of a cross-sectional shape of the beam based at least in part on the signals received from the first and second electrodes.

5. The apparatus of claim 3, wherein the processing unit is configured to move the beam, to adjust a shape of the beam, or both, based on the determined position of the beam.

6. The apparatus of claim 3, wherein the processing unit is configured to adjust an operation of an accelerator based on the determined position of the beam.

7. The apparatus of claim 1, further comprising a second beam position monitor coupled to the structure.

8. The apparatus of claim 7, wherein the first beam position monitor is configured to provide first signals for monitoring a first position of the beam along a first axis, and wherein the second position monitor is configured to provide second signals for monitoring a second position of the beam along a second axis that is different from the first axis.

9. The apparatus of claim 7, wherein the second beam position monitor comprises a third electrode and a fourth electrode, the third electrode being mounted to a third side of the structure, the fourth electrode being mounted to a fourth side of the structure, the fourth side being opposite from the third side.

10. The apparatus of claim 9, further comprising a third position monitor having a fifth electrode and a sixth electrode, wherein the third position monitor is downstream with respect to the first and second beam position monitors.

11. The apparatus of claim 10, further comprising a fourth position monitor having a seventh electrode and an eighth electrode, wherein the fourth position monitor is downstream with respect to the first and second beam position monitors.

12. The apparatus of claim 11, further comprising a processing unit configured to determine a first coordinate of a first cross section of the beam based on first signals from the first position monitor and second signals from the second position monitor;
wherein the processing unit is also configured to determine a second coordinate of a second cross section of the beam based on third signals from the third position monitor and fourth signals from the fourth position monitor.

13. The apparatus of claim 1, wherein the first beam position monitor is connected to a daughter card.

14. The apparatus of claim 1, further comprising a second beam position monitor that is downstream from the first beam position monitor.

15. The apparatus of claim 14, wherein the first electrode and the second electrode are aligned along a first radial axis that is perpendicular to a longitudinal axis of the lumen, and wherein the second beam position monitor comprises a third electrode and a fourth electrode aligned along a second radial axis that is different from the first radial axis.

16. The apparatus of claim 15, wherein the first radial axis and the second radial axis form a 45° angle.

17. The apparatus of claim 15, wherein the first radial axis and the second radial axis form a 90° angle.

18. The apparatus of claim 14, wherein the first beam position monitor is coupled upstream with respect to the beam-bender, and wherein the second beam position monitor is coupled to the beam-bender or downstream with respect to the beam-bender.

19. The apparatus of claim 1, further comprising a first amplifier coupled to the first electrode, and a second amplifier coupled to the second electrode.

20. The apparatus of claim 19, wherein the first amplifier is configured to provide a first logarithmic response, and wherein the second amplifier is configured to provide a second logarithmic response.

21. The apparatus of claim 20, further comprising a processing unit is configured to subtract the second logarithmic response from the first logarithmic response.

22. The apparatus of claim 1, wherein the first position monitor comprises a log-ratio beam position monitor.

23. The apparatus of claim 1, wherein the structure is a part of an accelerator, a transmission line, or a beam-bender.

24. A method of monitoring a position of a beam at a medical radiation machine that includes an accelerator, a beam bender downstream with respect to the accelerator, and a target for interaction with the beam to generate radiation, the beam comprising an electron beam, the method comprising:
obtaining a first signal from a first electrode;
obtaining a second signal from a second electrode, wherein the first electrode and the second electrode are on first opposite sides of a space in the medical radiation machine through which the beam is being delivered, wherein the signals are obtained from the first and second electrodes every 1 nanosecond to 10 microseconds; and
processing the first signal and the second signal to determine a first position of the beam;
wherein the first electrode and the second electrode are parts of a first position monitor, and wherein the first position monitor is located upstream with respect to a location where the radiation is generated; and
wherein the first position monitor comprising the first electrode and the second electrode is separated from the beam bender.

25. The method of claim 24, wherein the first position of the beam comprises a value of a coordinate.

26. The method of claim 24, further comprising:
obtaining a third signal from a third electrode;
obtaining a fourth signal from a fourth electrode; wherein the third electrode and the fourth electrode are on second opposite sides of the space through which the beam is being delivered; and
processing the third signal and the fourth signal to determine a second position of the beam.

27. The method of claim 26, wherein the first position of the beam comprises a first value, and the second position of the beam comprises a second value, and wherein the first value and the second value form a first coordinate for the beam.

28. The method of claim 27, wherein the first coordinate represents a position of a cross section of the beam.

29. The method of claim 27, further comprising:
obtaining a fifth signal from a fifth electrode;
obtaining a sixth signal from a sixth electrode; wherein the fifth electrode and the sixth electrode are downstream with respect to the first position monitor; and
processing the fifth signal and the sixth signal to determine a third position of the beam.

30. The method of claim 29, further comprising:
obtaining a seventh signal from a seventh electrode;
obtaining a eighth signal from an eighth electrode; and
processing the seventh signal and the eighth signal to determine a fourth position of the beam.

31. The method of claim 30, wherein the third position of the beam comprises a third value, and the fourth position of the beam comprises a fourth value, and wherein the third value and the fourth value form a second coordinate for the beam.

32. The method of claim 24, further comprising adjusting the beam based at least in part on the determined first position of the beam.

33. A method of monitoring a position of a beam at a medical radiation machine that includes an accelerator, a beam bender downstream with respect to the accelerator, and a target for interaction with the beam to generate radiation, the beam comprising an electron beam, the method comprising:
- obtaining a first signal from a first electrode;
- obtaining a second signal from a second electrode, wherein the first electrode and the second electrode are on first opposite sides of a space in the medical radiation machine through which the beam is being delivered; and
- processing the first signal and the second signal to determine a first position of the beam;
- wherein the first electrode and the second electrode are parts of a first position monitor, and wherein the first position monitor is located upstream with respect to a location where the radiation is generated;
- wherein the first position monitor comprising the first electrode and the second electrode is separated from the beam bender; and
- wherein the beam has a pulse duration, and wherein the signals are obtained from the first and second electrodes at every period that is a fraction of the pulse duration of the beam.

* * * * *